US012672841B2

(12) United States Patent
Lee et al.

(10) Patent No.: US 12,672,841 B2
(45) Date of Patent: Jul. 7, 2026

(54) DEVICE AND METHOD FOR DETERMINING EXTENT OF LIVER EXAMINATION

(71) Applicant: Research & Business Foundation SUNGKYUNKWAN UNIVERSITY, Suwon-si (KR)

(72) Inventors: Sukhan Lee, Suwon-si (KR); Tae Wook Kang, Suwon-si (KR); Jong Hwan Shin, Suwon-si (KR); Ji Soo Han, Suwon-si (KR); Jin Seong Cho, Suwon-si (KR)

(73) Assignee: Research & Business Foundation SUNGKYUNKWAN UNIVERSITY, Suwon-si (KR)

( * ) Notice: Subject to any disclaimer, the term of this patent is extended or adjusted under 35 U.S.C. 154(b) by 0 days.

(21) Appl. No.: 18/918,211

(22) Filed: Oct. 17, 2024

(65) Prior Publication Data

US 2025/0120670 A1 Apr. 17, 2025

(30) Foreign Application Priority Data

Oct. 17, 2023 (KR) ........................ 10-2023-0138610

(51) Int. Cl.
*A61B 8/08* (2006.01)
(52) U.S. Cl.
CPC ..................................... *A61B 8/08* (2013.01)
(58) Field of Classification Search
CPC ..... A61B 8/523; A61B 8/5223; A61B 8/5292; A61B 8/08
See application file for complete search history.

(56) References Cited

U.S. PATENT DOCUMENTS

| | | | | |
|---|---|---|---|---|
| 2019/0378606 A1* | 12/2019 | Kelly | ...................... | G01R 33/50 |
| 2021/0177373 A1* | 6/2021 | Xie | ........................ | G16H 50/30 |

FOREIGN PATENT DOCUMENTS

| | | |
|---|---|---|
| JP | 2021-531885 A | 11/2021 |
| KR | 10-2012-0108849 A | 10/2012 |
| KR | 10-2224627 B1 | 3/2021 |
| KR | 10-2023-0059454 A | 5/2023 |

OTHER PUBLICATIONS

Request for the Submission of an Opinion for Korean Patent Application No. 10-2023-0138610, dated Aug. 7, 2025.
Jonghwan Shin et al., "Real-Time Deep Recognition of Standardized Liver Ultrasound Scan Locations," Sensors 2023, May 17, 2023, 23, 4850.

* cited by examiner

*Primary Examiner* — Chao Sheng

(57) ABSTRACT

The present invention relates to a technology for recognizing and determining an extent of a liver being examined by an operator during an ultrasound liver examination. In one aspect, a method of determining an extent of liver examination performed by a device for determining an extent of liver examination may include receiving an ultrasound image taken of a region of a liver as input, extracting features from the ultrasound image, determining a cross-section of the liver for which the ultrasound image was taken on the basis of the extracted features, and determining an extent of liver examination taken in the ultrasound image on the basis of the determined cross-section of the liver.

15 Claims, 6 Drawing Sheets

1000

DEVICE FOR DETERMINING
EXTENT OF LIVER EXAMINATION

1100

PROCESSOR

1200

MEMORY

S2100

OBTAIN ULTRASOUND IMAGE OF REGION OF LIVER

S2200

EXTRACT FEATURES FROM ULTRASOUND IMAGE

S2300

DETERMINE CROSS-SECTION OF LIVER FOR WHICH
ULTRASOUND IMAGE WAS TAKEN

S2400

DETERMINE EXTENT OF LIVER EXAMINATION
INCLUDED IN ULTRASOUND IMAGE

S2500

OUTPUT EXTENT OF LIVER EXAMINATION

DEVICE AND METHOD FOR DETERMINING EXTENT OF LIVER EXAMINATION

CROSS-REFERENCE TO RELATED APPLICATION

This application is based on and claims priority from Korean Patent Application No. 10-2023-0138610, filed on Oct. 17, 2023, the disclosure of which is incorporated herein in its entirety by reference for all purposes.

TECHNICAL FIELD

The present invention relates to a technology for recognizing and determining an extent of a liver being examined by an operator during an ultrasound liver examination.

This study relates to the research on ICT Consilience Creative Program (No. 2710007880) according to a research project conducted with the support of the Information and Communication Planning and Evaluation Institute with funding from the Ministry of Science and ICT (Government) in 2024.

In addition, this study relates to the research on AI Graduate School Support Program at Sungkyunkwan University (No. 2710008628) according to a research project conducted with the support of the National Research Foundation of Korea with funding from the Ministry of Science and ICT (Government) in 2024.

BACKGROUND

Existing medical ultrasound examination equipment requires an EMT sensor attached or a CT image that has been taken in advance to recognize a site being examined. In addition, the EMT sensor may be burdensome to an operator due to the inconvenience of installing and using it externally and on a probe. Moreover, there is a problem of increasing the burden due to the high cost of the sensor. The CT image has been taken in advance is difficult to be applied in general due to the nature of most examinations that use only ultrasound.

DOCUMENTS OF RELATED ART (Korean Patent Application Publication) No. 10-2012-0108849—Method of image matching between ultrasound image and magnetic resonance image—

SUMMARY

The present invention is directed to providing a technology for recognizing and determining an extent of liver being examined by an operator using an ultrasound device.

In addition, the present invention is directed to providing an operator with an image of an extent of liver examination.

In addition, the present invention is directed to providing an image of detailed sites of a liver (extent of examination) being examined using an ultrasound device, according to Couinaud classification of hepatic subsegments.

In one aspect, a method of determining an extent of liver examination performed by a device for determining an extent of liver examination may include receiving an ultrasound image taken of a region of a liver as input, extracting features from the ultrasound image, determining a cross-section of the liver for which the ultrasound image was taken on the basis of the extracted features, and determining an extent of liver examination taken in the ultrasound image on the basis of the determined cross-section of the liver.

In some implementations, in the extracting of the features, features for the liver, blood vessels around the liver, and organs around the liver included in the ultrasound image are extracted.

In some implementations, in the determining of the cross-section of the liver for which the ultrasound image was taken, at least one site of the liver included in the ultrasound image is determined on the basis of the extracted features, and the cross-section of the liver is determined on the basis of the determined at least one site.

In some implementations, the cross-section of the liver is at least one of an epigastrium longitudinal scan, an epigastrium transverse scan, a right subcostal scan-hepatic portal vein, a right subcostal-hepatic right lobe transverse scan, a liver dome scan, a right subcostal scan-hepatic vein, a gallbladder longitudinal scan, an extrahepatic bile duct longitudinal scan, an intercostal scan of right lobe of liver including right hepatic portal vein, a right posterior intercostal scan, or a right lower liver and right renal cortex scan.

In some implementations, in the determining an extent of liver examination taken, one of the plurality of detailed sites is determined according to Couinaud classification of hepatic subsegments.

In another aspect, a device for determining an extent of liver examination may include a memory including instructions to execute a method of determining an extent of liver examination, and a processor configured to, by executing the instructions, receive an ultrasound image taken of a region of a liver as input, extract features from the ultrasound image, determine a cross-section of the liver for which the ultrasound image was taken on the basis of the extracted features, and determine a detailed site of the liver included in the ultrasound image on the basis of the extracted features and the determined cross-section of the liver.

According to one aspect of the present invention, it is possible to recognize and determine an extent of liver examination being examined by an operator using an ultrasound device.

In addition, the present invention is directed to making it possible to provide an operator with an image of an extent of liver examination.

In addition, the present invention is directed to making it possible to provide an image of detailed sites of a liver being examined using an ultrasound device, according to Couinaud classification of hepatic subsegments.

DETAILED DESCRIPTION

Advantages and features of the present disclosure and methods for achieving them will be made clear from the embodiments described below in detail with reference to the accompanying drawings. The present disclosure may, however, be embodied in many different forms, and should not be construed as being limited to the embodiments set forth herein. Rather, these embodiments are provided so that this disclosure will be thorough and complete, and will fully convey the scope of the present disclosure to those skilled in the art. The present disclosure is merely defined by the scope of the claims.

In describing the embodiments of the present disclosure, detailed descriptions of known functions or configurations will be omitted except when actually necessary in describing the embodiments of the present disclosure. In addition, terms to be described later are terms defined in consideration of functions in an embodiment of the present disclosure, which may vary according to a user's or operator's intention or practice. Therefore, the definition should be made based on the contents throughout this specification.

The terms such as "unit" and "-er" used hereinafter refer to one or more units for processing at least one function or operation, which may be implemented by hardware, software, or a combination thereof.

Figure 1:
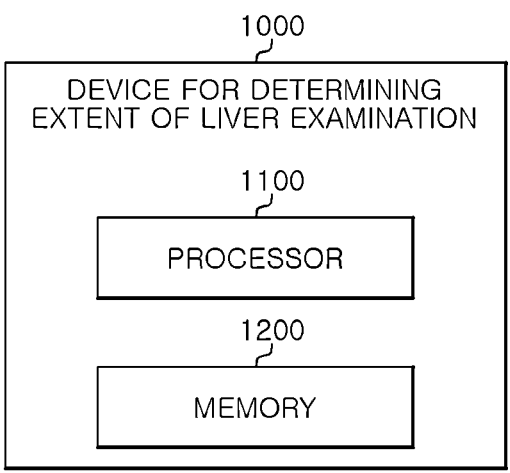
FIG. 1 is a block diagram of a device for determining an extent of liver examination according to an embodiment of the present invention.

FIG. 1 is a block diagram of a device for determining an extent of liver examination according to an embodiment of the present invention.

With reference to FIG. 1, a device 1000 for determining an extent of liver examination may include a processor 1100 and a memory 1200.

The processor 1100 may control an overall operation of the device 1000 for determining an extent of liver examination by executing instructions stored in the memory 1200 to determine the extent of liver examination.

The memory 1200 is executed by the processor 1100 and may control an overall operation of the device 1000 for determining an extent of liver examination and may store instructions used to determine the extent of liver examination.

A more detailed description of an operation of the device 1000 for determining an extent of liver examination will be described below with reference to FIGS. 2 to 6.

Figure 2:
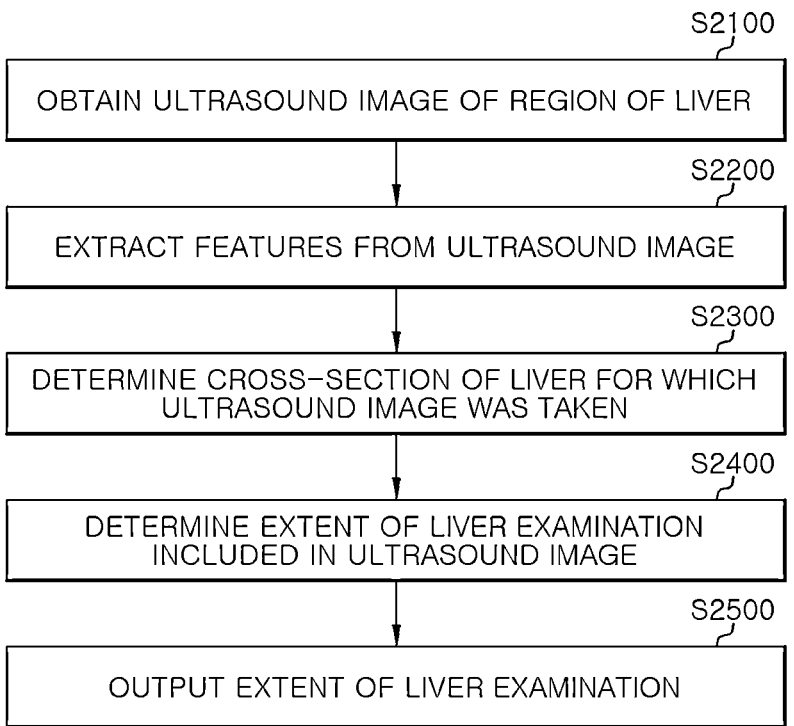
FIG. 2 is a flowchart of a method of determining an extent of liver examination according to an embodiment of the present invention.

FIG. 2 is a flowchart of a method of determining an extent of liver examination according to an embodiment of the present invention.

Hereinafter, the method will be described in terms of an example performed by the device 1000 for determining an extent of liver examination illustrated in FIG. 1.

In step S2100, the device 1000 for determining an extent of liver examination may obtain, by an operator such as a medical doctor, an ultrasound image of a region of a patient's liver from an external device (e.g., an ultrasound device, etc.) using an ultrasound device.

In an embodiment, the ultrasound image may include an image of a portion of a body, such as a liver, surrounding organs, and blood vessels.

In step S2200, the device 1000 for determining an extent of liver examination may extract features from the ultrasound image taken of the liver.

In an embodiment, the device 1000 for determining an extent of liver examination may extract features from the ultrasound image using a segmentation network, such as a deep learning model. Specifically, the device 1000 for determining an extent of liver examination may extract features for the liver, surrounding organs, blood vessels, and the like included in the ultrasound image.

In step S2300, the device 1000 for determining an extent of liver examination may determine a cross-section of the liver for which the ultrasound image was taken.

In an embodiment, the device 1000 for determining an extent of liver examination may determine a cross-section of the liver for which the ultrasound image was taken on the basis of features for the liver, surrounding organs, blood vessels, and the like extracted from the ultrasound image.

In an embodiment, the device 1000 for determining an extent of liver examination may determine one of a preset plurality of liver cross-sections. Here, the preset plurality of liver cross-sections may be liver cross-sections corresponding to at least one of standard images according to the Korean Medical Ultrasound Association and the like.

Figure 3:
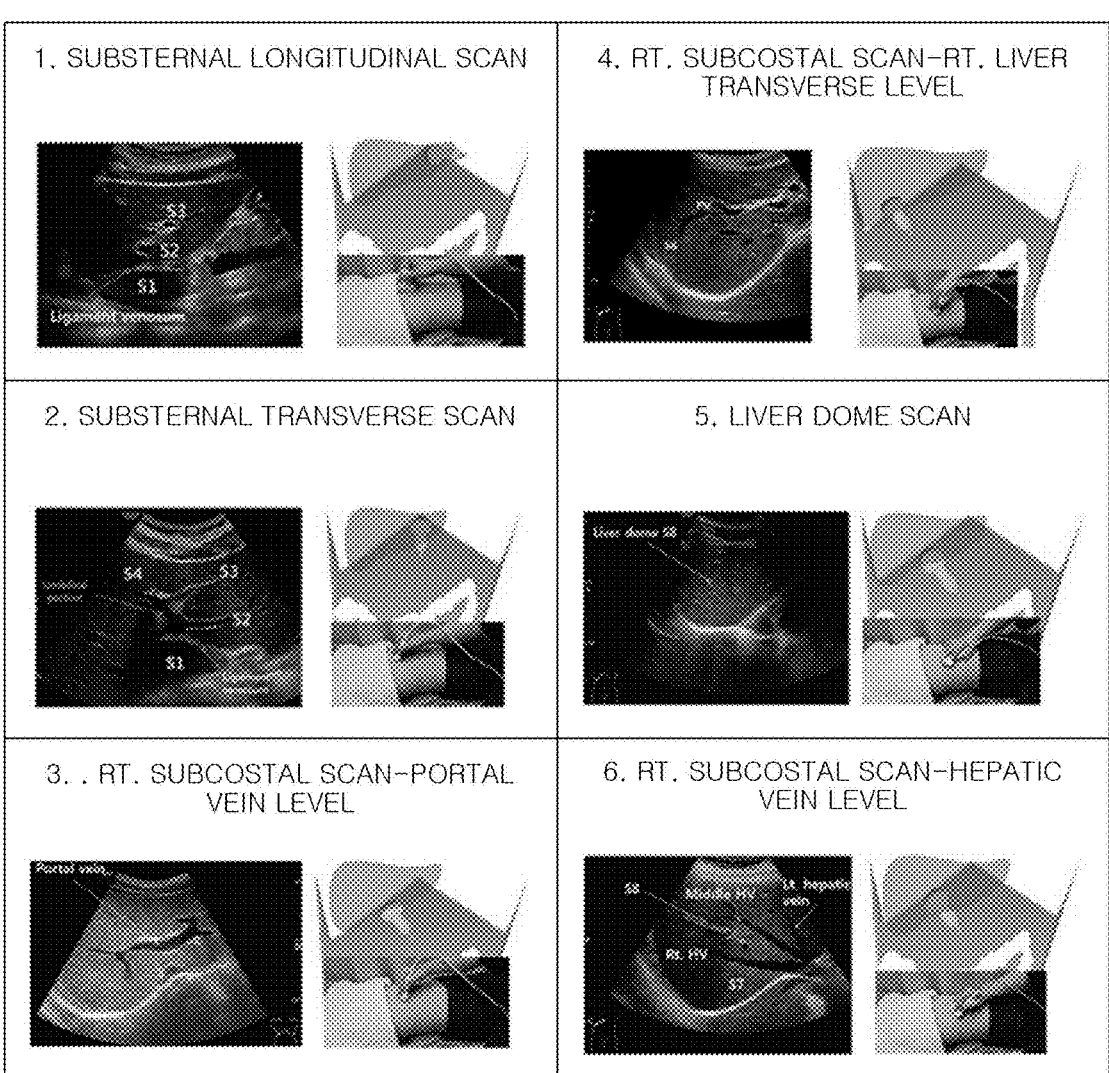
FIGS. 3 and 4 are drawings showing example of liver section in which ultrasound images were taken according to one embodiment of the present invention.
Figure 4:
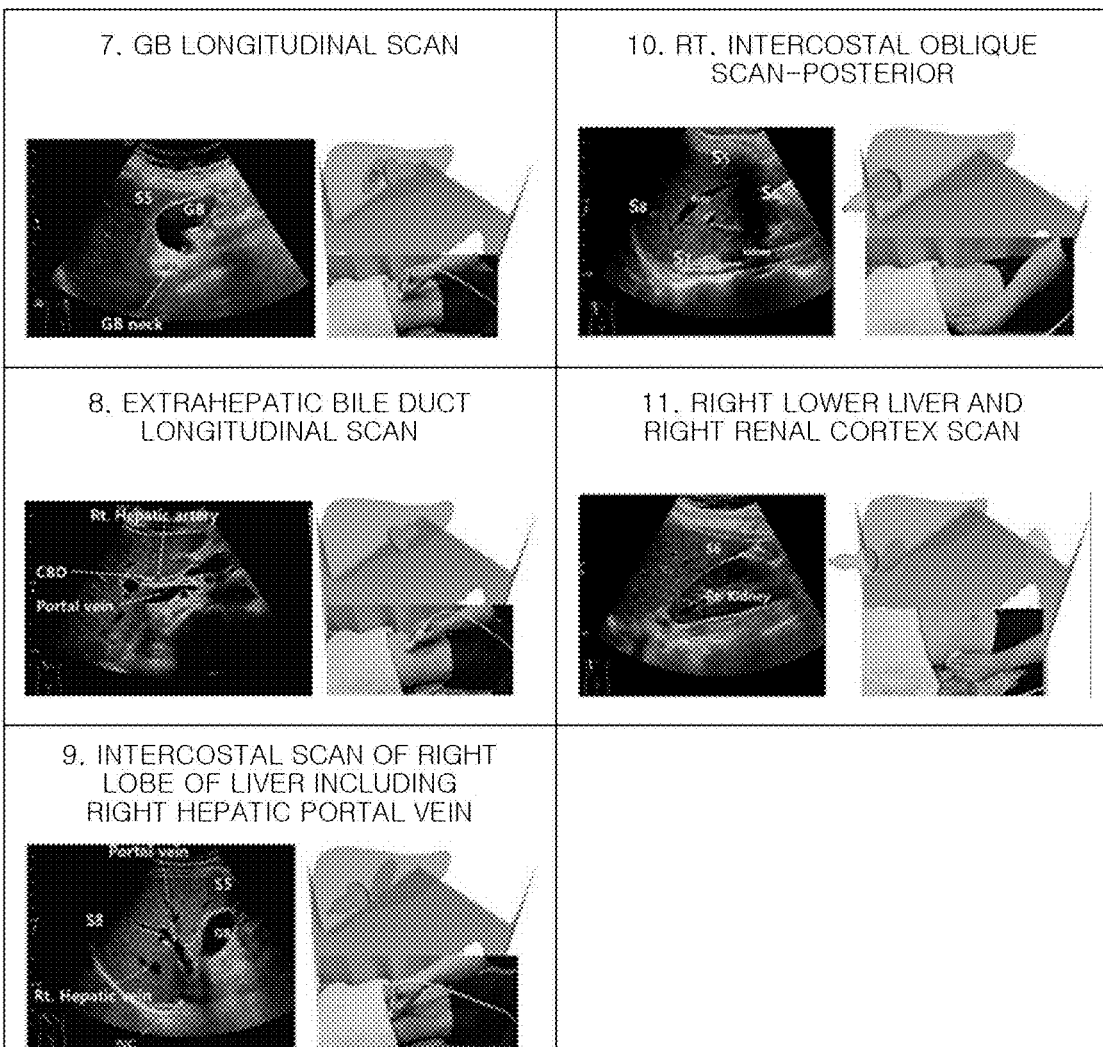

In an embodiment, the standard images may be an epigastrium longitudinal scan, an epigastrium transverse scan, a right subcostal scan-hepatic portal vein, a right subcostal-hepatic right lobe transverse scan, a liver dome scan, a right subcostal scan-hepatic vein, a gallbladder longitudinal scan, an extrahepatic bile duct longitudinal scan, an intercostal scan of right lobe of liver including right hepatic portal vein, a right posterior intercostal scan, and a right lower liver and right renal cortex scan, and the like, as illustrated in FIGS. 3 and 4.

In step S2400, the device 1000 for determining an extent of liver examination may determine detailed sites of the liver included in the ultrasound image on the basis of a cross-section of the liver for which the ultrasound image was taken.

In an embodiment, the device 1000 for determining an extent of liver examination may determine detailed sites of the liver included in the ultrasound image on the basis of features extracted from the ultrasound image and a cross-section of the liver for which the ultrasound image was taken.

Figure 5:
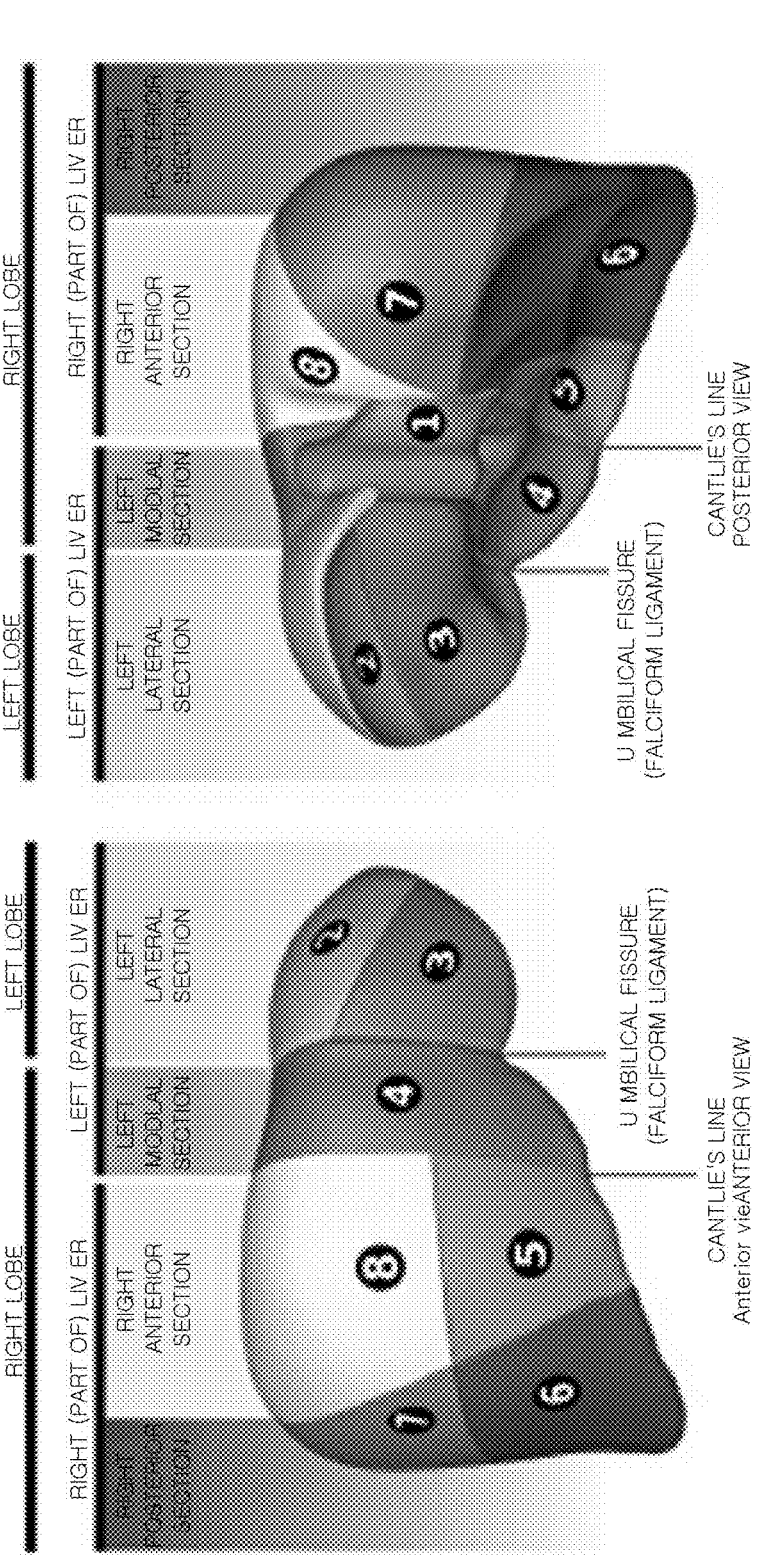
FIG. 5 is a drawing showing detailed parts of the liver according to one embodiment of the present invention.

In an embodiment, the detailed sites of the liver may refer to one of the sites of the liver according to Couinaud classification of hepatic subsegments, as illustrated in FIG. 5.

In step S2500, the device 1000 for determining an extent of liver examination may output the detailed sites of the liver included in the ultrasound image.

In an embodiment, the device 1000 for determining an extent of liver examination may output a 3D model of the sites of the liver to be visually recognized by an operator and the like.

In an embodiment, the device 1000 for determining an extent of liver examination may output an anatomical image corresponding to the detailed sites of the liver included in the ultrasound image.

In addition, the device 1000 for determining an extent of liver examination may determine a cross-section of the liver for which the ultrasound image is taken on the basis of a pre-learned image processing model to predict a cross-section of the liver being examined from the ultrasound image.

In addition, the device 1000 for determining an extent of liver examination may determine detailed sites of the liver using a pre-learned model to predict the detailed sites of the liver included in the ultrasound image on the basis of a cross-section of the liver for which the ultrasound image was taken.

Figure 6:
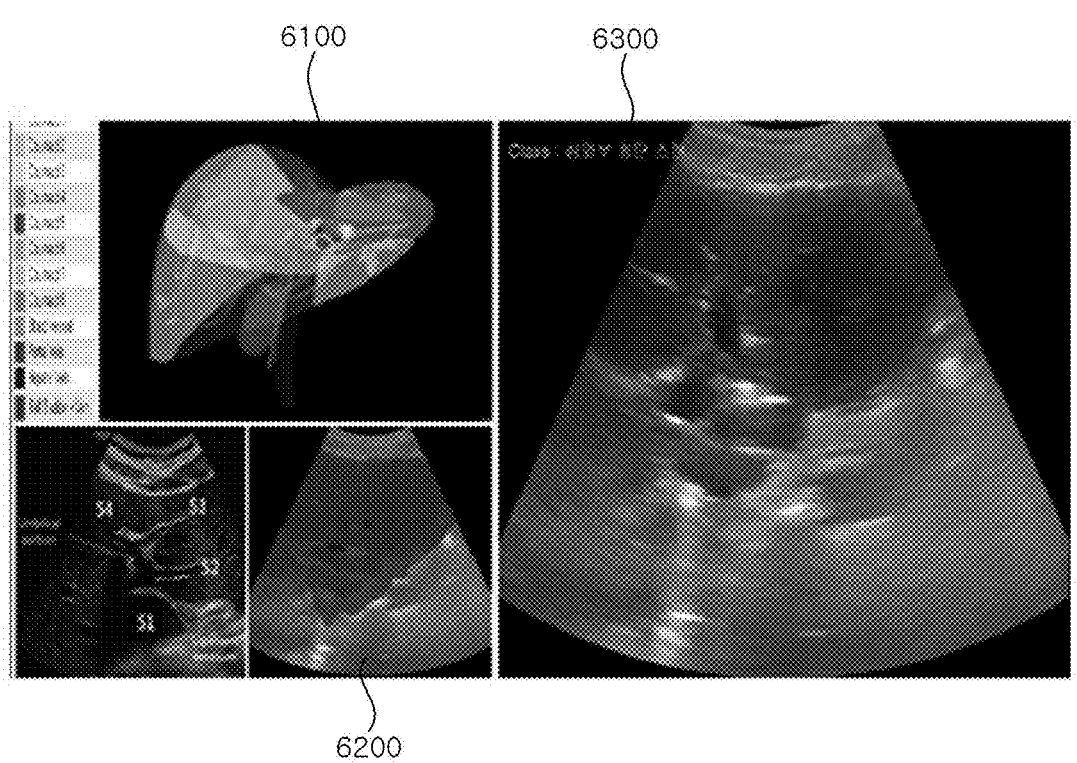
FIG. 6 is a view for describing an example of outputting an extent of liver examination according to an embodiment of the present invention.

FIG. 6 is a view for describing an example of outputting an extent of liver examination according to an embodiment of the present invention.

With reference to FIG. 6, the reference numeral 6100 indicates an example of detailed sites of the liver included in the ultrasound image expressed as a 3D model according to Couinaud classification of hepatic subsegments. Therefore, the operator may anatomically recognize a site of the liver being examined using ultrasound equipment.

The reference numeral 6200 indicates information on the liver, surrounding organs, blood vessels, and the like included in the ultrasound image. Therefore, the operator may clearly distinguish between the liver to be examined and other surrounding organs.

The reference numeral 6300 indicates the ultrasound image. It is because this is information that needs obviously to be provided to the operator who is using the ultrasound device.

Figure 7:
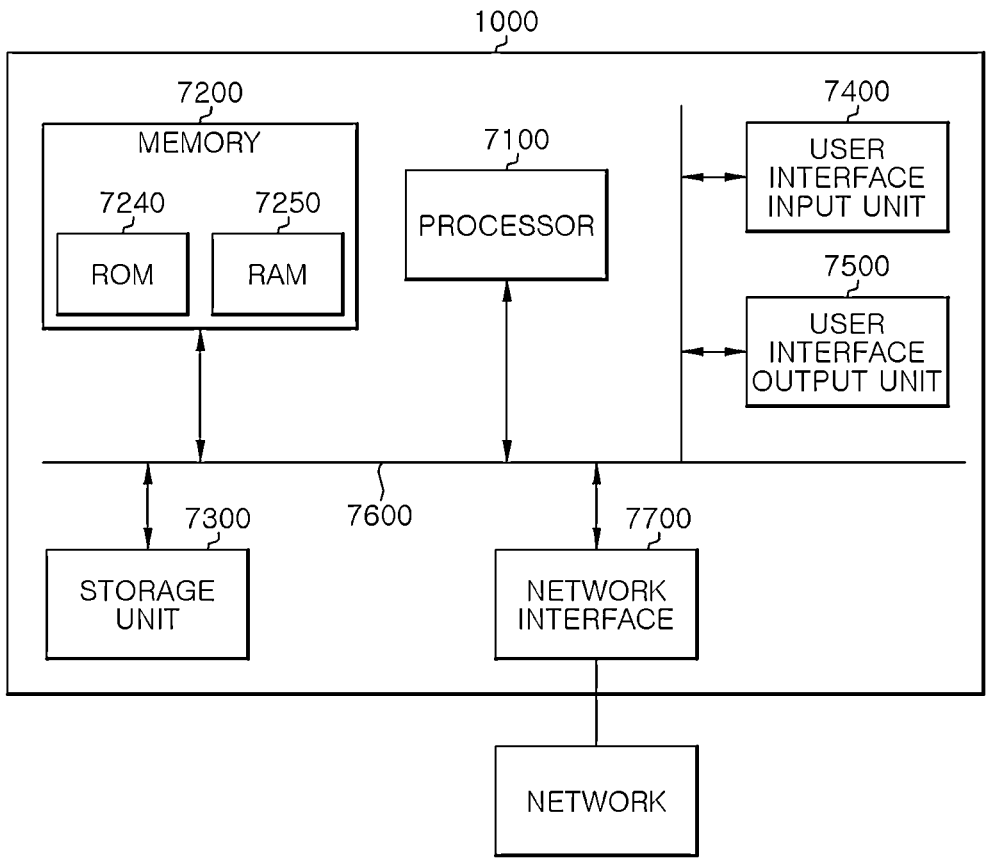
FIG. 7 is a block diagram of a device for determining an extent of liver examination according to another embodiment of the present invention.

FIG. 7 is a block diagram of a device for determining an extent of liver examination according to another embodiment of the present invention.

As illustrated in FIG. 7, the device 1000 for determining an extent of liver examination may include at least one of elements of a processor 7100, a memory 7200, a storage unit 7300, a user interface input unit 7400, or a user interface output unit 7500, which may communicate with each other through a bus 7600. In addition, the device 1000 for determining an extent of liver examination may also include a network interface 7700 to connect to a network. The processor 7100 may be a CPU or semiconductor device that executes processing instructions stored in the memory 7200 and/or the storage unit 7300. The memory 7200 and the storage unit 7300 may include various types of volatile and non-volatile memory media. For example, the memory may include a ROM 7240 and a RAM 7250.

The apparatus described above may be implemented as a hardware component, a software component, and/or a combination of hardware components and software components. For example, the apparatus and components described in the embodiments may be achieved using one or more general purpose or special purpose computers, such as, for example, a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and one or more software applications executing on the operating system.

In addition, the processing device may access, store, manipulate, process, and generate data in response to execution of the software. For ease of understanding, the processing device may be described as being used singly, but those skilled in the art will recognize that the processing device may include a plurality of processing elements and/or a plurality of types of processing elements. For example, the processing device may include a plurality of processors or one processor and one controller. Other processing configurations, such as a parallel processor, are also possible.

The software may include a computer program, a code, an instruction, or a combination of one or more thereof, and the processing device may be configured to be operated as desired or commands may be made to the processing device independently or collectively. The software and/or data may be permanently or temporarily embodied in any type of machine, a component, a physical device, virtual equipment, a computer storage medium or device, or a signal wave transmitted in order to be interpreted by the processing device or to provide an instruction or data to the processing device. The software may be dispersed on a computer system connected to a network, to be stored or executed in a dispersive method. The software and data may be stored in one or more computer readable recording media.

The above description is merely exemplary description of the technical scope of the present invention, and it will be understood by those skilled in the art that various changes and modifications can be made without departing from original characteristics of the present invention. Therefore, the embodiments disclosed in the present specification are provided for illustrative purposes only but not intended to limit the technical spirit of the present invention. The scope of the technical spirit of the present invention is not limited thereby. The protection scope of the present invention should be interpreted based on the following claims and it should be appreciated that all technical scopes included within a range equivalent thereto are included in the protection scope of the present invention.

DETAILED DESCRIPTION OF MAIN
ELEMENTS

1000: DEVICE FOR DETERMINING EXTENT OF
LIVER EXAMINATION
1100: PROCESSOR
1200: MEMORY

What is claimed is:

1. A method of determining an extent of liver examination performed by a device for determining the extent of the liver examination, the method comprising:
    receiving an ultrasound image taken of a region of a liver as input;
    extracting features from the ultrasound image;
    determining one of a plurality of preset cross-sections of the liver for which the ultrasound image was taken on the basis of the extracted features; and
    determining a detailed site among a plurality of detailed sites of the liver examination taken in the ultrasound image on the basis of the determined one of the plurality of preset cross-sections of the liver.

2. The method of claim 1, wherein in the extracting of the features, features for the liver, blood vessels around the liver, and organs around the liver included in the ultrasound image are extracted.

3. The method of claim 1, wherein each of the plurality of preset cross-sections of the liver is at least one of an epigastrium longitudinal scan, an epigastrium transverse scan, a right subcostal scan-hepatic portal vein, a right subcostal-hepatic right lobe transverse scan, a liver dome scan, a right subcostal scan-hepatic vein, a gallbladder longitudinal scan, an extrahepatic bile duct longitudinal scan, an intercostal scan of right lobe of liver including right hepatic portal vein, a right posterior intercostal scan, or a right lower liver and right renal cortex scan.

4. The method of claim 1, wherein in the determining the detailed site of the liver examination taken, one of the plurality of detailed sites is determined according to Couinaud classification of hepatic subsegments.

5. The method of claim 1, wherein the determining of the one of the plurality of preset cross-sections of the liver includes classifying the ultrasound image into one of at least eleven predefined standard liver scan views.

6. The method of claim 1, wherein the determining of the one of the plurality of preset cross-sections is based on a spatial relationship between the liver and at least one surrounding organ or blood vessel identified in the extracted features.

7. The method of claim 1, wherein extracting features from the ultrasound image comprises applying a deep learning-based segmentation network to the ultrasound image to perform pixel-wise labeling of anatomical structures.

8. A device for determining an extent of liver examination, the device comprising:

a memory including instructions to execute a method of determining the extent of the liver examination; and a processor configured to, by executing the instructions, receive an ultrasound image taken of a region of a liver as input, extract features from the ultrasound image, determine one of a plurality of preset cross-sections of the liver for which the ultrasound image was taken on the basis of the extracted features, and determine a detailed site among a plurality of detailed sites of the liver included in the ultrasound image on the basis of the determined one of the plurality of preset cross-sections of the liver.

9. The device of claim 8, wherein the processor is configured to extract features for the liver, blood vessels around the liver, and organs around the liver included in the ultrasound image.

10. The device of claim 8, wherein each of the plurality of preset cross-sections of the liver is at least one of an epigastrium longitudinal scan, an epigastrium transverse scan, a right subcostal scan-hepatic portal vein, a right subcostal-hepatic right lobe transverse scan, a liver dome scan, a right subcostal scan-hepatic vein, a gallbladder longitudinal scan, an extrahepatic bile duct longitudinal scan, an intercostal scan of right lobe of liver including right hepatic portal vein, a right posterior intercostal scan, or a right lower liver and right renal cortex scan.

11. The device of claim 8, wherein the processor is configured to determine one of the plurality of detailed sites according to Couinaud classification of hepatic subsegments.

12. A non-transitory computer-readable recording medium storing a computer program, the computer program comprising instructions, when executed by a processor, to allow the processor to perform a method of determining an extent of liver examination, the method including:

receiving an ultrasound image taken of a region of a liver as input;

extracting features from the ultrasound image;

determining one of a plurality of preset cross-sections of the liver for which the ultrasound image was taken on the basis of the extracted features; and determining a detailed site among a plurality of detailed sites of the liver examination taken in the ultrasound image on the basis of the determined one of the plurality of preset cross-sections of the liver.

13. The non-transitory computer-readable recording medium of claim 12, wherein in the extracting of the features, features for the liver, blood vessels around the liver, and organs around the liver included in the ultrasound image are extracted.

14. The non-transitory computer-readable recording medium of claim 12, wherein each of the plurality of preset cross-sections of the liver is at least one of an epigastrium longitudinal scan, an epigastrium transverse scan, a right subcostal scan-hepatic portal vein, a right subcostal-hepatic right lobe transverse scan, a liver dome scan, a right subcostal scan-hepatic vein, a gallbladder longitudinal scan, an extrahepatic bile duct longitudinal scan, an intercostal scan of right lobe of liver including right hepatic portal vein, a right posterior intercostal scan, or a right lower liver and right renal cortex scan.

15. The non-transitory computer-readable recording medium of claim 12, wherein in the determining the detailed site of the liver examination taken, one of the plurality of detailed sites is determined according to Couinaud classification of hepatic subsegments.

* * * * *